United States Patent
Baynham

(10) Patent No.: US 10,610,370 B2
(45) Date of Patent: *Apr. 7, 2020

(54) POLYAXIAL CANNULATED SCREW

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 130 days.

This patent is subject to a terminal disclaimer.

(21) Appl. No.: 15/942,730

(22) Filed: Apr. 2, 2018

(65) Prior Publication Data

US 2018/0221162 A1 Aug. 9, 2018

Related U.S. Application Data

(63) Continuation-in-part of application No. 15/695,521, filed on Sep. 5, 2017, now Pat. No. 9,931,221, which is a continuation of application No. 14/210,262, filed on Mar. 13, 2014, now Pat. No. 9,763,802.

(60) Provisional application No. 61/784,573, filed on Mar. 14, 2013.

(51) Int. Cl.
| | |
|---|---|
| *A61B 17/70* | (2006.01) |
| *A61F 2/44* | (2006.01) |
| *A61B 17/86* | (2006.01) |
| *A61B 17/88* | (2006.01) |
| *A61F 2/30* | (2006.01) |
| *A61F 2/46* | (2006.01) |

(52) U.S. Cl.
CPC .............. *A61F 2/441* (2013.01); *A61B 17/70* (2013.01); *A61B 17/7037* (2013.01); *A61B 17/7097* (2013.01); *A61B 17/864* (2013.01); *A61B 17/8811* (2013.01); *A61F 2/442* (2013.01); *A61F 2/30744* (2013.01); *A61F 2/4611* (2013.01); *A61F 2002/3085* (2013.01); *A61F 2002/30563* (2013.01); *A61F 2002/30588* (2013.01); *A61F 2002/444* (2013.01)

(58) Field of Classification Search
CPC . A61B 17/70; A61B 17/7001; A61B 17/7032; A61B 17/7037; A61B 17/7097; A61B 17/864; A61B 17/8805; A61B 17/8811; A61B 2017/00898
USPC .................................................. 606/246–279
See application file for complete search history.

(56) References Cited

U.S. PATENT DOCUMENTS

| | | |
|---|---|---|
| 6,022,350 A | 2/2000 | Ganem |
| 7,789,896 B2 | 9/2010 | Jackson |
| 7,905,908 B2 | 3/2011 | Cragg et al. |
| 8,308,777 B2 | 11/2012 | Assell et al. |
| 9,763,802 B2 | 9/2017 | Baynham |
| 2005/0113919 A1* | 5/2005 | Cragg ................ A61B 17/70 623/17.11 |
| 2008/0188895 A1 | 8/2008 | Cragg et al. |

(Continued)

*Primary Examiner* — Si Ming Ku
(74) *Attorney, Agent, or Firm* — McHale & Slavin, P.A.

(57) ABSTRACT

A polyaxial cannulated screw having a resilient expandable body capable of supporting compressive and cyclic loads. The expandable body provides an artificial disc prosthesis by use of the expandable body that mimics the properties of the natural disc by maintaining the intervertebral disc space through a full range of natural motion, absorbing shocks and permitting a natural range of motion. A U-shaped saddle attached to a spherical ball permits optimum positioning of a rod member by polyaxial placement.

13 Claims, 4 Drawing Sheets

(56) References Cited

U.S. PATENT DOCUMENTS

| | | |
|---|---|---|
| 2009/0099609 A1* | 4/2009 | Froehlich ............ A61B 17/7097 606/301 |
| 2009/0099610 A1 | 4/2009 | Johnson et al. |
| 2010/0331898 A1 | 12/2010 | Froehlich |
| 2011/0040329 A1 | 2/2011 | Ainsworth et al. |
| 2013/0010054 A1 | 1/2013 | Sunkara et al. |
| 2013/0046351 A1 | 2/2013 | Schwappach |
| 2013/0096634 A1* | 4/2013 | Suh .................... A61B 17/7097 606/304 |
| 2013/0245602 A1 | 9/2013 | Sweeney |
| 2014/0277468 A1 | 9/2014 | Baynham |
| 2015/0362099 A1 | 12/2015 | Aramaki et al. |

\* cited by examiner

POLYAXIAL CANNULATED SCREW

PRIORITY CLAIM

In accordance with 37 C.F.R. 1.76, a claim of priority is included in an Application Data Sheet filed concurrently herewith. Accordingly, the present invention claims priority as a continuation-in-part to U.S. patent application Ser. No. 15/695,521, filed on Sep. 5, 2017, entitled "CANNULATED SCREW WITH BALLOON", which is a continuation to U.S. patent application Ser. No. 14/210,262, filed on Mar. 13, 2014, entitled "TRANSPEDICULAR NUCLEUS REPLACEMENT SYSTEM", now U.S. Pat. No. 9,763,802, issued Sep. 19, 2017, which claims priority to U.S. provisional patent application Ser. No. 61/784,573, filed on Mar. 14, 2013, entitled "TRANSPEDICULAR NUCLEUS REPLACEMENT SYSTEM", the contents of which are hereby expressly incorporated herein by reference.

FIELD OF THE INVENTION

The present invention relates generally to surgically-implantable spinal devices and more specifically, to a cannulated screw with inflatable expandable body for support of a rod.

BACKGROUND OF THE INVENTION

Intervertebral discs are oblate spherical structures that maintain the space between adjacent vertebrae. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc wherein a mucoprotein gel serves to absorb shocks.

Deterioration of an intervertebral disc results in limited mobility and can cause severe pain. For instance, normal aging causes the nucleus pulposus to lose fluid and contract in volume resulting in a reduction in the intervertebral space. Any reduction of space between adjacent vertebrae may put pressure on the nerves of the spinal column. Further, a reduction in volume of the nucleus pulposus reduces the disc's ability to absorb shock which can result in disc herniation. The bulge of a herniated disc may also put pressure on nearby nerve structures resulting in pain as well as diminished range of motion.

Surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc.

The use of an expandable body like artificial disc prosthesis filled with a polymer is known. A joint arthroplasty device can be formed in situ by inserting a hollow device having an aperture and a lumen into a target joint, and injecting material into the hollow device to form an implant. An artificial/prosthetic facet joint with expandable body joint space component composed of latex, polymer, silicone or the like materials.

What is lacking in the field is a cannulated screw that includes an inflatable expandable body to mimic the properties of the natural disc by maintaining the intervertebral disc space through a full range of natural motion and absorb the shocks of daily use.

SUMMARY OF THE INVENTION

A polyaxial cannulated screw includes a resilient expandable body structure capable of supporting compressive and cyclic loads. The various embodiments of the present invention may be implanted in an anterior, anterior-lateral, or a posterior surgical approach to the procedure. The size of each implant component (in collapsed form) is small enough to be inserted with minimal incisions. In particular, the polyaxial cannulated screw provides an immediate benefit for those installations employing a rod between facets.

Accordingly, it is an objective of the invention to provide an artificial disc prosthesis by use of a cannulated screw for inclusion of a expandable body that mimics the properties of the natural disc by maintaining the intervertebral disc space through a full range of natural motion, absorbs the shocks and permits a natural range.

Another objective of the invention is to provide an artificial disc prosthesis that is anchored to the vertebral body through the pedicle and is coupled to a U-shaped saddle for support of a rod member.

Still another objective of the invention is to provide an artificial disc prosthesis that is anchored with a expandable body mechanism to the vertebral body and is coupled to a polyaxial attached U-shaped saddle for support of a rod member.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
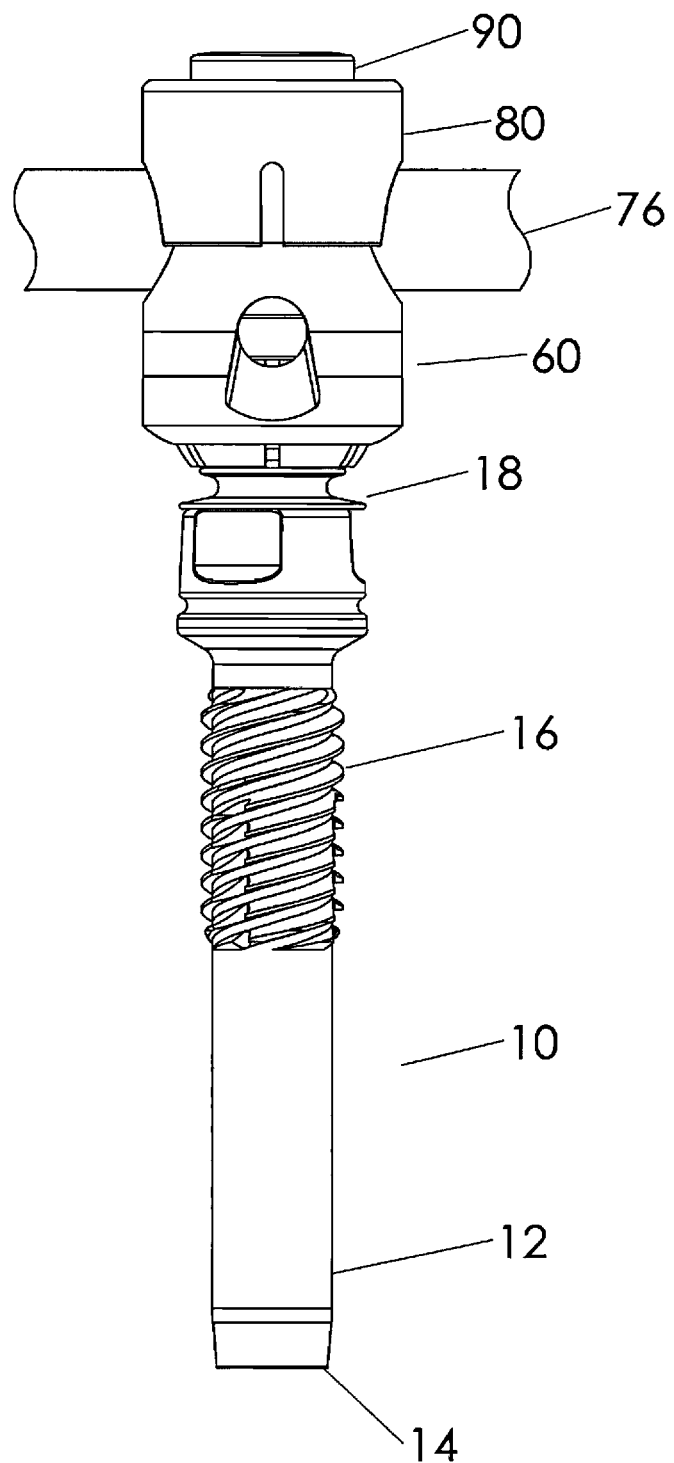
FIG. 1 is a side view of the cannulated screw of the instant invention.
Figure 2:
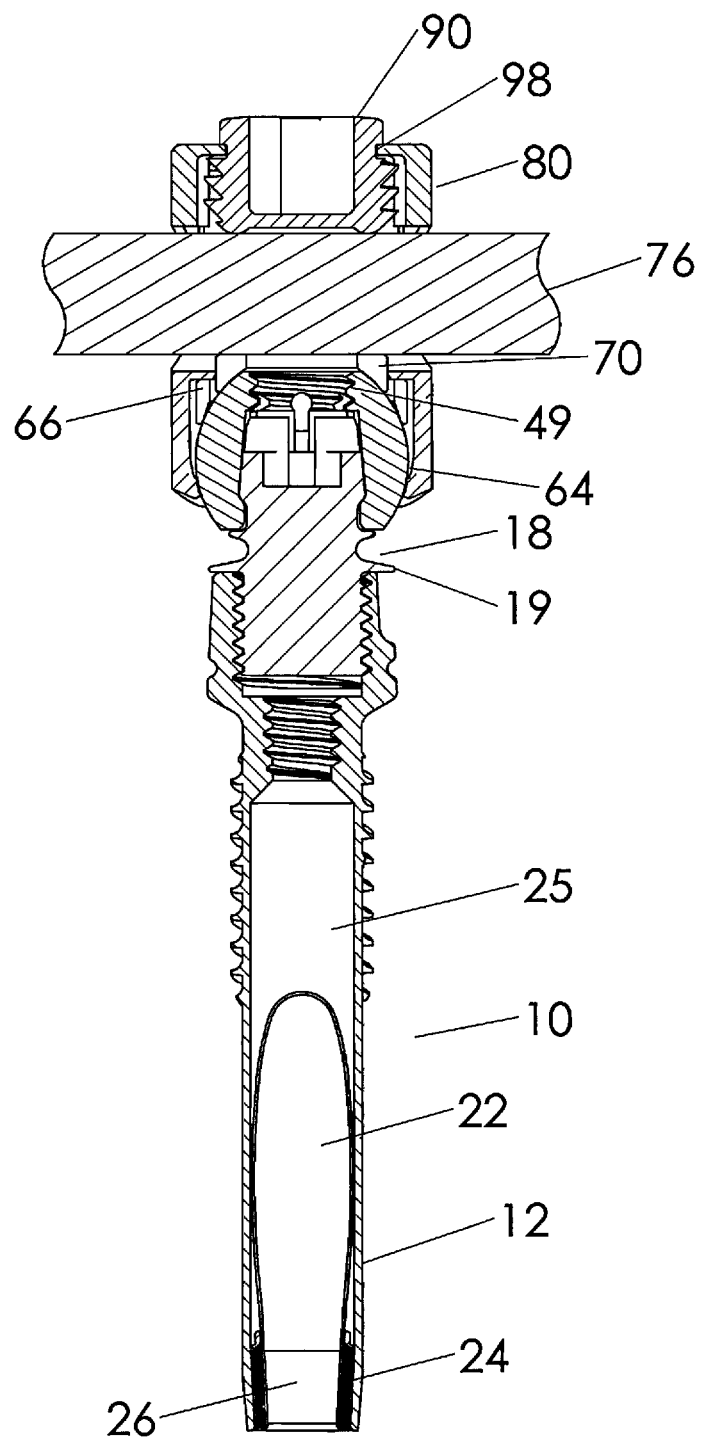
FIG. 2 is a cross sectional view thereof.

The medical device enables surgical access to the weight-bearing portion of the spine percutaneously through the pedicle. The medical device described herein comprises a cannulated screw that includes an inflatable expandable body to mimic the properties of the natural disc by maintaining the intervertebral disc space through a full range of natural motion and absorb the shocks of daily use. An end of the screw includes a U-shaped saddle for securing a rod member. The U-shaped saddle can be fixed or polyaxially attached.

The medical device described herein provides a better overall approach to modifying the relationship between adjacent vertebral bodies, without altering the surrounding anatomy, thereby reducing the time a patient and surgeon have to spend in surgery, and reducing or altogether eliminating hospitalization following the procedure. Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions: The terminology used herein is for the purpose of describing particular embodiments only and is not intended to be limiting of the invention. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The following description of the preferred embodiments is merely exemplary in nature and is in no way intended to limit the invention, its application or uses.

Now referring to the Figures, set forth is the cannulated screw 10 of the instant invention comprising a hollow body 12 having an open end 14. An expandable body 22 (for example, a balloon) in stored in a cavity 25 formed within the hollow body 12. The term "balloon" will be used merely as a descriptive term, however, it is understood that any expandable body may be used. The expandable body extends upward through the hollow body 12 which allows insertion of the cannulated screw 10 through a pedicle thereby shielding the expandable body 22 during insertion. A ferrule 24 fits within an open end 26 of the expandable body 22 creating a seal between the expandable body and the inner surface of the hollow body 12. The cannulated screw comprises external threading, the hollow body 12 includes external threading 23 along the upper portion 38 and extending for about one half to about a quarter of the length of the hollow body 12.

Figure 3:
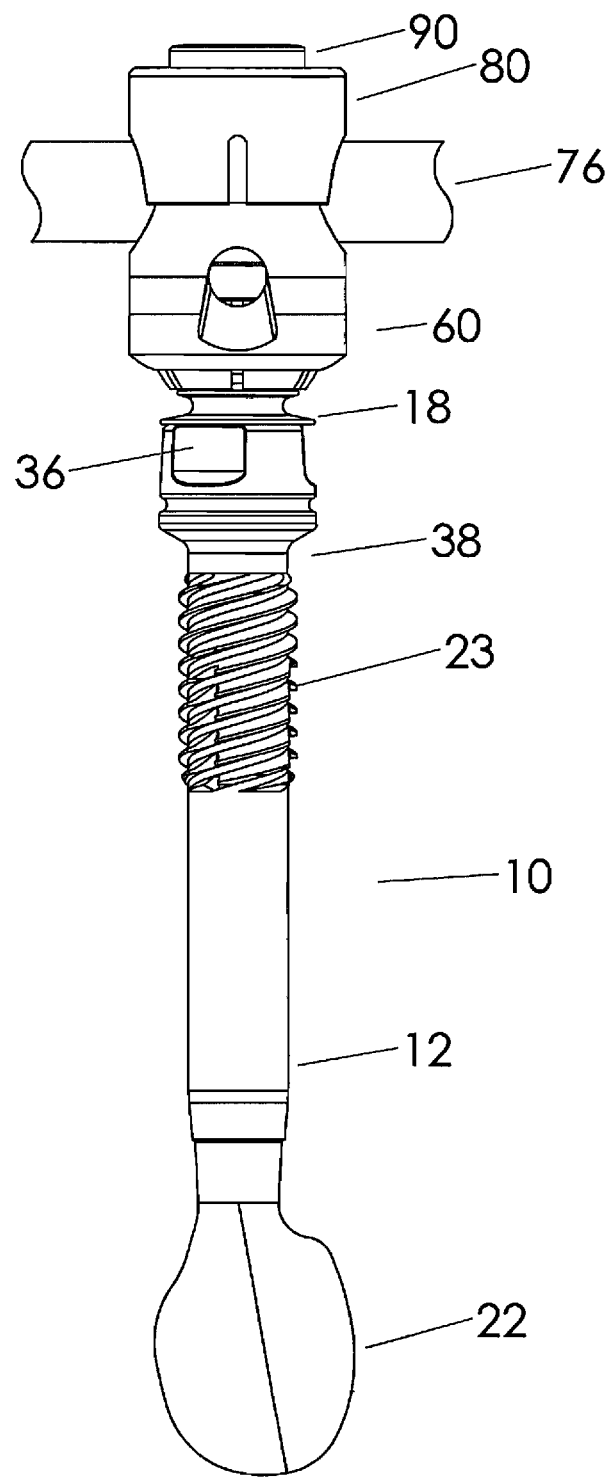
FIG. 3 is a side view thereof depicting the expandable body in an inflated position.
Figure 4:
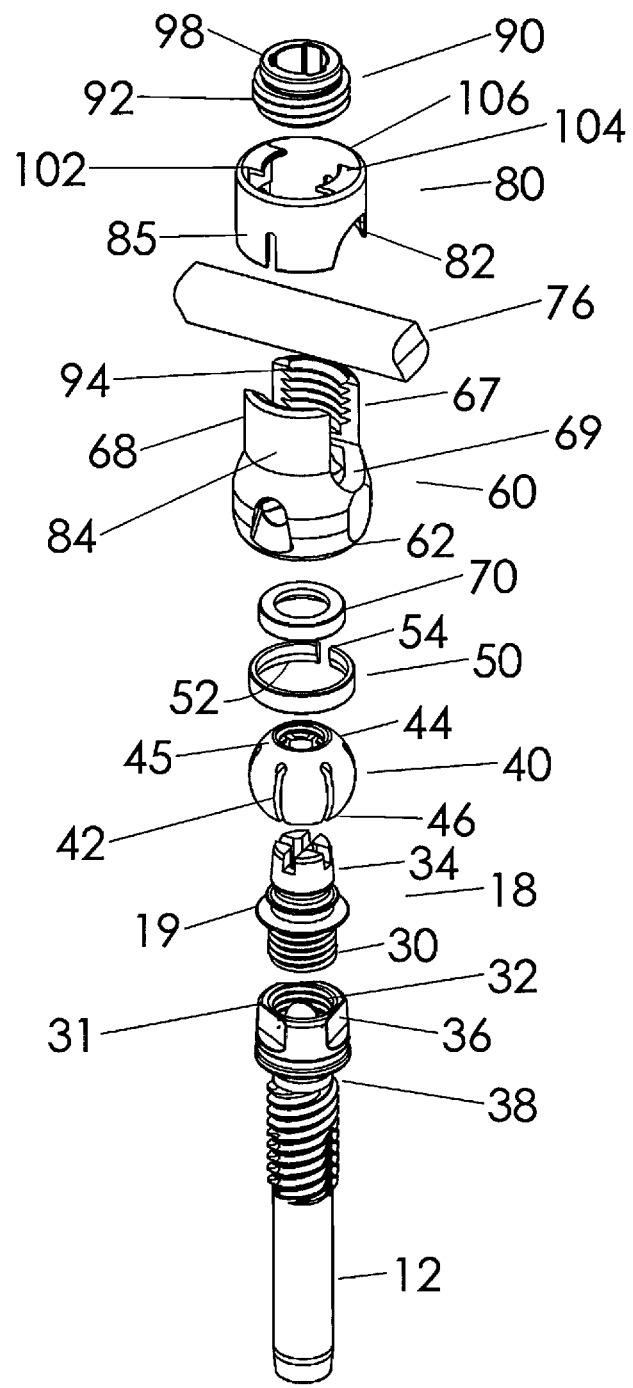
FIG. 4 is an exploded view thereof.

The expandable body 22 is formed of an expandable material. The expanding of the expandable body 22 is accomplished by insertion of a volumetric material into the cavity 25 through threaded inlet 32. As material is inserted in the cavity 25, the expandable body 22 is pushed outward from open end 26. The cap 18 includes a lower threaded section 30 for engaging reciprocal threaded inlet 32 of the hollow body 12. An upper section 34 of the cap is slotted for receipt of an installation driver head, not shown. The installation driver is used to rotate the cap 18 for attachment to the hollow body 12. Side surfaces 36 along an upper portion 38 of the hollow body 12 are constructed and arranged to receive a socket like wrench for holding the hollow body 12 as the cap 18 is secured thereto. As illustrated in FIG. 3, the expandable body 22 is shown in a deployed position. Once the expandable body 22 is filled with material, the cap 18 is threaded onto the reciprocal threads 32 to secure the material within the expandable body. The cap 18 includes an enlarged lip 19 that to further seal material, the enlarged lip 19 engaging the upper edge 31 of the hollow body 12. An o-ring seal may be included, not shown, to reduce or eliminate the need for the enlarged lip 19.

The expandable body is filled with biological agents or other material, delivered to the expandable body from the open second end of the cannulated screw. The expandable body may be constructed from any of a variety of flexible materials, thereby enabling the expandable body to expand and contract to a variety of sizes. Suitable volumetric materials can be viscous and non-viscous including saline, gels, latex, polymers, polyethylenes, silicones, polyurethanes, metallics, ceramics, collagen, hydrogels. Volumetric materials can be radio-opaque contrast agents, allowing fluoroscopic viewing during injection into the disc to a known pressure.

In a preferred embodiment, a spherical ball element 40 is coupled to the cap 34 during manufacturing. The spherical ball element 40 having slots 42 formed along a continuous sidewall 44 extending from a lower portion 46 and discontinuing along at a predetermined distance along an upper portion 45 of the spherical ball element 40. The slots 42 allowing the lower portion 46 of the spherical ball element 40 to change in diameter upon the application of compression from split ring 50 positioned around an outer diameter of the ball element 40. The split ring 50 includes an inner taper 52 for engaging the spherical ball element 40 when an upper edge 54 is compressed upon securement of a set screw 90 explained later in this specification. The spherical ball element 40 having a threaded aperture 47 along the upper portion 45 receptive to a positioning screw 49 constructed and arranged to prevent compression of the spherical ball element 40 along the upper portion 45 when the lower portion 46 is compressed.

A U-shaped saddle 60 having a base 62 is constructed and arranged to fit over an outer diameter 64 of the spherical ball element 40. The U-shaped saddle 60 having an inner wall 66 sized to engage the upper edge 54 of the split ring 50. A spacer 70 is positioned over a top portion of the split ring 40 to assure a rod member is compressed directly onto the spherical ball element 40. The spacer 70 having a central aperture 71 to allow an installation driver to engage the cap 18 during installation. During installation, the spherical ball element allows polyaxial movement of the U-shaped saddle 60 for optimum aligning of a rod member 76. The U-shaped saddle 60 having first sidewall 68 and second sidewall 68 with a lower surface 69 that combine to receive the rod member 76. The use of a rod member 76 is a common and conventional method of adjoining portions of an individual's injured or diseased spine. It should be noted that the spherical ball member can be removed and the U-shaped saddle 60 coupled directly to the cap 18 providing a fixed position for the attachment of a rod member 76.

A compression ring 80 employs rod openings 82 to accommodate the rod member 76. A sidewall 85 of the compression ring is constructed and arranged to be placed over the outer surface 84 of the U-shaped member 60 sidewalls 67, 68 thereby utilizing the sidewalls to reinforce the compression ring wherein the thickness of the compression ring can be reduced. Set screw 90 has a thread 92 sized to engage the inner threaded surface 94 of first sidewall 67 and second sidewall 68. The set screw further includes a rim 98 for engaging rim tabs 102 and 104 formed along the top edge 106 of the compression ring 80.

In operation, the threaded portion 23 of the hollow body is positioned through a pedicle wherein the expandable body 22 is deployed by the injection of a fluid within the cavity 25 fluidly coupled to the expandable body 22. Once the hollow body is stabilized the cap 17 is attached to the hollow body 12 for securing the expandable body 22 in the deployed position. Attached to the cap 18 is the U-shaped saddle 60 secured to a spherical ball element 40. The U-shaped saddle 60 is attached to the spherical ball element 40 allowing polyaxial movement wherein a rod member 60 can be placed within the U-shaped saddle 60 in an optimum position so as to along with other vertebra to be coupled together by the rod member 60. Once the rod member is positioned, the compression ring 80 is secured over the rod member 76 and sidewalls 67 and 68 of the U-shaped saddle 60 and secured thereto by set screw 90. It is noted that upon attachment of the set screw 90, the U-shaped saddle 60 applies compression pressure to the spherical ball member 40 which in turn applies compression pressure to the cap 18 thereby locking the rod member in a fixed position eliminating all polyaxial movement while the set screw is attached.

In other embodiments, the device functions as artificial disc prosthesis. In preferred embodiments, the device is manufactured from biocompatible components. It is noted that the medical device described herein may be used for percutaneous pedicle access, as well as vertebroplasty and kyphoplasty surgeries.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A cannulated screw comprising: a hollow body with an open first end and an open second end, an expandable body secured to said open first end with a ferrule element, said expandable body extending entirely into said hollow body when in a non-deployed position and extending out of said hollow body when volumetric material is directed through said open second end causing expansion of said expandable body in a deployed position, a cap attached to said open second end, and a U-shaped saddle; wherein said cap secures the volumetric material in the expandable body and said U-shaped saddle is constructed and arranged for securing a rod member to said cap.

2. The cannulated screw of claim 1, wherein said ferrule is inserted in an open end of the expandable body forming a seal between said open first end of the hollow body and said expandable body.

3. The cannulated screw of claim 1, wherein said open second end comprises threads for receiving said cap, said cap includes threads for temporarily receiving a dispenser for use in inserting volumetric material into said expandable body.

4. The cannulated screw of claim 1, wherein volumetric material comprises a biological agent delivered to said expandable body from said open second end of the hollow body.

5. The cannulated screw of claim 1, wherein the cannulated screw comprises external threading, the external threading extending from said open second end and extending for one half to a quarter of a length of the cannulated screw.

6. The cannulated screw of claim 1, wherein said open second end comprises a terminal end having a diameter greater than the hollow body for receiving a locking plug.

7. The cannulated screw of claim 1, wherein said volumetric material is viscous or non-viscous.

8. The cannulated screw of claim 1, wherein said volumetric material is selected from the group comprising saline, gels, latex, polymers, polyethylenes, silicones, polyurethanes, metallics, ceramics, collagen, and hydrogels.

9. The cannulated screw of claim 1, wherein said volumetric material includes radio-opaque contrast agents permitting fluoroscopic viewing.

10. The cannulated screw of claim 9, wherein fluoroscopic viewing during injection of the volumetric material into said expandable body permits visual determination of material pressure with said expandable body.

11. The cannulated screw of claim 1, wherein U-shaped member is attached to said cap by a spherical ball element, said spherical ball element allowing polyaxial rotation of said U-shaped member.

12. The cannulated screw of claim 1, including a compression ring securable to said U-shaped member by a set screw, said compression ring including at least one rim tab for engaging a rim formed on said set screw.

13. The cannulated screw of claim 11, including a split ring transferring a compression force from said U-shaped saddle to said spherical ball element.

* * * * *